United States Patent [19]
Knorr et al.

[11] Patent Number: 5,869,668
[45] Date of Patent: Feb. 9, 1999

[54] PROCESSES FOR PREPARING [L]- OR [D]-HOMOALANIN-4-YL-(METHYL) PHOSPHINIC ACID AND SALTS THEREOF BY RACEMATE RESOLUTION

[75] Inventors: Harald Knorr, Frankfurt; Günter Schlegel, Liederbach; Herbert Stark, Kelkheim, all of Germany

[73] Assignee: Hoechst Schering AgrEvo GmbH, Berlin, Germany

[21] Appl. No.: 49,404

[22] Filed: Mar. 27, 1998

Related U.S. Application Data

[62] Division of Ser. No. 398,216, Mar. 2, 1995, Pat. No. 5,767,309.

[30] Foreign Application Priority Data

Mar. 4, 1994 [DE] Germany .......................... 44 07 197.3

[51] Int. Cl.$^6$ ....................................................... C07F 9/30
[52] U.S. Cl. ............................................ 546/35; 546/134
[58] Field of Search ...................................... 546/134, 35

[56] References Cited

U.S. PATENT DOCUMENTS

| | | |
|---|---|---|
| 3,213,106 | 10/1965 | Sasaji et al. . |
| 4,265,654 | 5/1981 | Takematsu et al. . |
| 4,647,692 | 3/1987 | Jacewicz . |
| 4,777,279 | 10/1988 | Zeiss . |
| 4,922,006 | 5/1990 | Zeiss . |
| 5,229,379 | 7/1993 | Marescaux ................................ 562/11 |
| 5,374,736 | 12/1994 | Zeiss . |

FOREIGN PATENT DOCUMENTS

| | | |
|---|---|---|
| 2065128 | 10/1992 | Canada . |
| 2075151 | 2/1993 | Canada . |
| 2085145 | 6/1993 | Canada . |
| 0224880 | 6/1987 | European Pat. Off. . |
| 0238954 | 9/1987 | European Pat. Off. . |
| 0346658 | 12/1989 | European Pat. Off. . |
| 0499376 | 8/1992 | European Pat. Off. . |
| 0508296 | 10/1992 | European Pat. Off. . |
| 0530506 | 3/1993 | European Pat. Off. . |
| 0546556 | 6/1993 | European Pat. Off. . |
| 28 56 260 | 7/1979 | Germany . |
| 39 20 570 | 1/1991 | Germany . |
| 39 23 650 | 1/1991 | Germany . |
| 551945 | 7/1974 | Switzerland . |

OTHER PUBLICATIONS

Bull. Chim. Soc. Jap., vol. 56 (1993), pp. 3744–3747.
Chem. Lett. (1990), pp. 233–234.
J. Org. Chem. 1983, 48, pp. 843–846 by Yamada et al.
Gal, et al., J. Org. Chem., vol. 42, No. 2, pp. 142–143 (1997).

Japanese Application No. 4–213445 published Apr. 8, 1992.

English language abstract of DE OS 39 20 570.

English language abstract of DE OS 39 23 650.

Chemical Abstracts, vol. 68, No. 3, Jan. 15, 1968, Columbus, Ohio, Abstract No. 13342, by S. Yoshikawa et al. entitled "The Racemization of 1–Glutamic Acid by the Catalytic Action of Alicyladehyde Derivatives in the Presence of Metal Ion", pp. 331–336.

Bulletin of the Chemical Society of Japan, vol. 51, No. 8, 1978, Tokyo, Japan, by M. Ando & S. Emoto entitled "Catalytic Activities of Saliclaldehyde Derivatives VIII. Kinetic Studies of Catalytic Racemization of Glutamic Acid at 25 C", pp. 2366–2368.

Bulletin of the Chemical Society of Japan, vol. 41, No. 9, 1969, Tokyo, Japan by M. Ando & S. Emoto entitled "Catalytic Activities of Salicylaledehyd Derivatives: II. Kinetic Studies of the Racemization of Amino Acid", pp. 2628–2631.

Bulletin of the Chemical Society of Japan, vol. 36, No. 6, 1963, Tokyo, Japan by Toi et al. entitled "Synthesis Resins Catalyzing the Racemization of Amino Acids, I. The Preparation of the Resins", pp. 734–738.

Chemical Abstracts, vol. 91, No. 24, Dec. 10, 1979, Columbus, Ohio, Abstract No. 193857v by I.A. Yamskov et al. entitled "Preparation of Poly(acylamidosalicyladehyde) and the Study of its Ability to Catalyze the Racemization of Optically Active Amino Acids".

Journal of the Medical Chemical Society, vol. 76, 1954, Washington, by Ikawa et al. entitled Benze Analogs of Pyridoxal. The Reactions of 4–Nitrosalicylaldehyde with Amino Acids, pp. 653–655.

*Primary Examiner*—Robert Gerstl
*Attorney, Agent, or Firm*—Frommer Lawrence & Haug LLP

[57] ABSTRACT

The title compounds are obtained by racemate resolution of D,L-homoalanin-4-yl(methyl)phosphinic acid via precipitation of one of the diastereomeric salts using chiral bases such as quinine or cinchonine. It is possible to increase the yield of desired enantiomer by transformed racemate resolution when the precipitation of the diastereomeric salt takes place with the racemization of the undesired enantiomer in the presence of (hetero)—aromatic aldehydes. The racemization method is also suitable for structurally different optically active amino acids.

9 Claims, No Drawings

PROCESSES FOR PREPARING [L]- OR [D]-HOMOALANIN-4-YL-(METHYL) PHOSPHINIC ACID AND SALTS THEREOF BY RACEMATE RESOLUTION

This application is a divisional of Ser. No. 08/398,216 filed Mar. 2, 1995 now U.S. Pat. No. 5,767,309.

[DL]-Homoalanin-4-yl(methyl)phosphinic acid (DL-Ia) and the ammonium salt thereof (DL-Ib) are amino-acid derivatives with herbicidal activity (DE-A-27 17 440). The amino-acid derivatives are active in the L form (L-Ia or L-Ib), whereas the relevant enantiomeric D form is virtually inactive (DE-A-2856260).

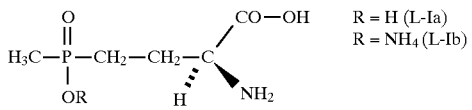

In order to be able to use the pure active substance, special processes have been developed to prepare [L]-homoalanin-4-yl(methyl)phosphinic acid and the ammonium salt thereof.

According to DE-A-3 920 570 and DE-A-3 923 650, the L form can be obtained by enzymatic transamination. However, the working up of the transamination solution is technically very elaborate; in addition, large amounts of salt are produced.

According to EP-A-224 880, the pure L form is likewise obtained by starting from [D]-valine in several stages, with an enantioselective alkylation of [R]-3-isopropyl-2,5-dialkoxy-3,6-dihydropyrazines as key reaction; however, the disadvantages for application on the industrial scale are the difficulty of obtaining the heterocyclic intermediates and the necessity to use organometallic agents.

In addition, the L form is obtained by asymmetric hydrogenation of N-substituted 2-amino-4- [(methyl) (hydroxy)-phosphino]butenoic acids (EP-A-238954).

It is likewise possible to prepare (L-Ia) starting from L-vinylglycine or (subst.) L-4-vinyl-1,3-oxazolidin-5-ones and methanephosphonous monoesters (EP-A-546566 and EP-A-346658); however, the chiral precursors are not easy to obtain.

Furthermore, processes using methanephosphonous diesters are known (EP-A-508298 and EP-A-530506); however, the required phosphorous component is not available in large amounts, which impedes implementation of this process on the large scale.

Practicable separation of the racemic mixture [DL-Ia] into the pure enantiomers by the "classical" precipitation method utilizing differences in the solubilities of diastereomeric salts has not been disclosed to date. Some processes in which racemates can be separated with the aid of chiral compounds via diastereomeric salts have been described for structurally different amino acids. Of particular interest in this connection are processes in which the precipitation of a diastereomeric salt of the desired enantiomer is combined with racemization of the undesired enantiomer.

For example, Bull. Chim. Soc. Jap. 56 (1983) 3744–3747 describes the preparation of [D]-phenylglycine from [DL]-phenylglycine with the aid of [d]-camphor-10-sulfonic acid as salt former in the presence of acetic acid and salicylaldehyde as racemizing agent in 68% yield and an optical purity of 95.9%.

Shiraiwa et al. describe in Chem. Lett. 1990, 233 et seq. a process for preparing N-methyl- [D]-2-phenylglycine from N-methyl-[DL]-2-phenylglycine using [1]-camphorsulfonic acid in butanoic acid without the addition of aldehydes or ketones. in this case the salt of the D-amino acid precipitates while the L-amino acid racemizes. Triethylamine is subsequently used to liberate the D-amino acid from the diastereomeric salt in yields of 71–77%.

U.S. Pat. No. 4,647,692 describes the racemate resolution of the amino acids 4-hydroxyphenylglycine and 3,4-dihydroxy-phenylglycine by precipitation using (+)-3-bromocamphor-10-sulfonic acid in the presence of ketones and organic acids such as acetic acid. This method is also recommended in general form for racemate resolution of DL-Ia.

Independently of the above precipitation methods which combine racemate resolution and racemization of the incorrect enantiomer, publications which describe only racemization methods are known:

J. Org. Chem. 48 (1983) 843–846 relates to the racemization of D-amino acids in acetic acid or other organic carboxylic acids in the presence of catalytic amounts of aliphatic or aromatic aldehydes.

U.S. Pat. No. 3213106 discloses the racemization of optically active amino acids in water without the addition of strong bases or acids at temperatures of 150°–250° C.; furthermore, according to JP-42-13445, amino acids can be racemized in water and in the presence of an aliphatic aldehyde with metal ion catalysis. The latter racemization methods have the disadvantage that the amino acids are partly decomposed at the stated temperatures or the conversion rate is much too low.

Application of the precipitation methods mentioned hereinbefore to the separation of [DL]-homoalanin-4-yl-(methyl)phosphonic acid using d- or l-camphorsulfonic acid or derivatives thereof proves to be impracticable. For example, it is not possible to separate out the diastereomeric salt of [L]-homoalanin-4-yl(methyl)-phosphinic acid and [d]-3-bromocamphor-10-sulfonic acid, as is evident from Comparative Examples A) and B) (see section "Comparative Examples").

The object therefore was to find a racemate resolution process which can be carried out on the industrial scale and with which the disadvantages described above are substantially avoided.

The invention relates to a process for preparing [L]-homoalanin-4-yl(methyl)phosphinic acid (L acid) and salts thereof or [D]-homoalanin-4-yl(methyl)phosphinic acid (D acid) and salts thereof from racemic [DL]-homoalanin-4-yl (methyl)phosphinic acid (DL acid) or salts thereof, which comprises a) reacting DL acid or salt thereof with a chiral base,
b) allowing the salt of the L acid or D acid and of the chiral base to crystallize out of a solution of the resulting mixture of the diastereomeric salts of D acid, L acid and the chiral base in an aqueous or aqueous-organic solvent in which the salt of the D acid or of the L acid has a higher solubility than the salt of the L acid or D acid, respectively (racemate resolution) and
c) in the case where the free L acid or D acid is prepared, neutralizing the resulting salt with an acid, or in the case where a salt other than that obtained according to b) is prepared, carrying out a metathesis.

The process according to the invention for preparing [L]-homoalanin-4-yl(methyl)phosphonic acid and salts thereof is carried out with chiral bases, preferably alkaloid bases such as quinine, cinchonidine and brucine. The use of quinine is particularly advantageous.

The enantiomers of the said chiral bases, for example quinidine and cinchonine, are suitable for preparing [D]-homoalanin-4-yl(methyl)phosphinic acid.

Because of the greater economic importance of the L acid, the process routes are described hereinafter for the example of the preparation of L acid. The processes can be used analogously to prepare the D acid by using the enantiomeric chiral bases.

In order to reduce the solubility of diastereomeric salts of the [L] form compared with the solubility in pure aqueous solutions it is possible to use, for example, solvent mixtures composed of water and organic solvents which are miscible with water in the particular mixing ratio used. Suitable mixing partners for the aqueousorganic solvent mixtures are, for example, organic solvents from the group consisting of alcohols such as, for example, methanol, ethanol, n-propanol, i-propanol, n-butanol, i-butanol, sec-butanol and t-butanol, of ketones such as, for example, acetone, methyl ethyl ketone, methyl isobutyl ketone and N-methylpyrrolidone, and combinations of the said solvents. It is also possible with comparatively small amounts of solvent, i.e. using highly concentrated solutions, to use water as sole solvent.

The use of i-propanol or t-butanol in combination with water proves particularly advantageous.

The optimal temperature for the crystallization depends on the chiral base, the solvent, the concentration of the salt, the amount of the chiral base and the crystallization rate. It is, as a rule, advantageous to carry out the crystallization at temperatures of 0°–100° C., preferably 0°–85° C., in particular at 15°–75° C. Suitable and preferred solvent mixtures are composed of water and alcohols, for example t-butanol:water in the ratio of, for example, 20:80 to 90:10, preferably 50:50 to 85:15, in particular 70:30 to 85:15, or isopropanol:water in the ratio of 20:80 to 90:10, preferably 50:50 to 90:10, in particular 70:30 to 85:15. The latter ratios of amounts preferably apply to carrying out the crystallization at temperatures of 0°–85° C., in particular 15°–75° C.

The liberation of the acid (L-Ia) from the diastereomeric salt of the crystals can take place in analogy to customary methods, for example by neutralization with an organic or inorganic acid, where appropriate in a suitable solvent. The metathesis into another salt can take place by reaction with an excess of an inorganic base which contains the desired cation, or with an organic base (for example amine base) or ammonia when optionally substituted ammonium salts of (L-Ia) are to be prepared. Preparation of the ammonium salt (L-Ib), which can be used satisfactorily as herbicide, by metathesis with ammonia is preferred. The reaction with ammonia can be carried out, for example, by dissolving the crystals in a suitable solvent such as methanol and passing in ammonia or adding a solution of ammonia in a solvent, for example methanol again, in excess, and precipitating the ammonium salt (L-Ib). The mother liquor which contains the chiral base can then be returned to the next batch.

In a preferred procedure for the process according to the invention, the undesired D isomer (D-Ia) or the salt thereof, for example the salt of (D-Ia) with the chiral base, is racemized, and the resulting racemic compound (DL-Ia) or salt thereof is used for the racemate resolution according to the invention.

Processes suitable in principle for the racemization of (D-Ia) are those with which other amino acids can also be racemized. For example, the references already mentioned above, Bull. Chim. Soc. Jap. 56 (1983) 3744–3747, Chem. Lett. 1990, 233 et seq. and J. Org. Chem. 48 (1983) 843–846 disclose the catalysis of racemizations of optically active amino acids by aldehydes in organic acids.

The racemization may take place separately or with the racemate resolution:

a) Suitable for carrying out the racemization of the D isomer after the crystallized salt of the L isomer has been separated out are the abovementioned processes (see also Example C in the "Comparative Examples" section hereinafter). Apart from the additional process stages in the case of separate racemization, however, the known processes usually have further disadvantages, for example that the racemization must take place in the presence of acids. The addition of organic acids has considerable technical disadvantages for the process when the known method is applied to the racemization of the salt of the D isomer and of the chiral base which results according to the invention in the mother liquor of the crystallization stage. Addition of acid means, for example, a change of the solvent, for which reason the racemization solution cannot be returned directly to the next crystallization batch without altering the crystallization conditions.

b) If, furthermore, the racemization of the D isomer is to take place in the same reaction mixture at the same time as the crystallization, according to the invention, of the salt of the L isomer and of the chiral base, the known racemization methods can no longer be applied or are not practicable industrially, as is evident from Comparative Example D hereinafter. Although the diastereomeric salt of (D-Ia) and of the chiral base, in this case quinine, can be smoothly racemized in acetic acid in the presence of salicylaldehyde (Comparative Example C), it is impossible to crystallize the diastereomeric salt of (L-Ia) in acetic acid medium (Comparative Example D).

The organic acids added in the known racemization methods must for the abovementioned reasons be avoided in the preferred combined crystallization process according to the invention. Racemization in the presence of the known aldehydes does not as a rule take place without the addition of acids, i.e. if the intention is to carry out the racemization with the aldehydes in neutral or weakly basic or even weakly acidic aqueous medium.

Surprisingly, our experiments have shown that the racemization takes place even in such media when certain aldehydes are used.

The invention therefore also relates to a novel process for the racemization of optically active amino acids, preferably amino acids of the formula (D-Ia) and derivatives thereof, which comprises reacting the optically active amino acids in the presence of six-membered (hetero)aromatic aldehydes which have a hydroxyl group in position 2 with respect to the aldehyde group and electron-attracting radicals such as, for example, $NO_2$, CN, $CF_3$ and $SO_3H$, in particular $NO_2$, in position 3 or 5 with respect to the aldehyde group and are further substituted where appropriate, in aqueous or aqueous-organic medium.

The racemization according to the invention takes place without the addition of inorganic or organic acids. Racemization in neutral or weakly basic or weakly acidic medium, for example at pH 4–9, in particular at pH 5–8, is preferred.

The racemization is, as a rule, carried out at temperatures of 0°–120° C., preferably 30°–85° C., in particular 35°–75° C., depending on the reactivity of the aldehyde.

Preferred aldehydes for the racemization are salicylaldehydes activated on the phenyl ring by electron-attracting radicals in position 3 or 5, for example nitro groups, and are further substituted where appropriate, for example 5-nitrosalicylaldehyde or 3,5-dinitrosalicylaldehyde.

It is also possible, for example, to use analogous heteroaromatic aldehydes in place of the aromatic aldehydes. It is worth mentioning in this connection pyridinealdehydes, for example pyridoxal, which may, depending on the substitution pattern, also be immobilized on an inorganic or organic support.

Suitable amino acids are the customary optically active amino acids and salts thereof, for example D- or L-alanine, substituted D- or L-alanines, substituted glycines such as phenylglycine or hydroxyphenylglycine, and D- or L-leucines etc. and the amino-acid derivatives such as (D-or L-Ia).

The amount of aldehydes used can vary within wide limits and can easily be optimized in preliminary experiments. The aldehydes are preferably used in less than the stoichiometric amount based on the amino acid or salt thereof, in particular in catalytic amounts. As a rule, the amounts of the particular aldehyde are in the range from 0.01 mole to 0.1 mole per mole of amino acid or salt thereof used. If a very small amount of aldehyde is used, the conversion takes place too slowly for practical purposes. The use of excessively large amounts of aldehyde may impair further processing of the mixture and also appears to have little sense from the economic viewpoint.

A particular advantage of the racemization according to the invention is that it can be carried out at considerably lower temperatures than was to be expected. The conversion not only takes place at the temperatures of 80°–150° C. used in strongly acidic media but can also be carried out at temperatures below 80° C., preferably 35°–75° C., in particular 40°–70° C. In contrast to the conventional methods mentioned, these low temperatures for the racemate resolution of (DL-Ia) using chiral bases make it possible to carry out the crystallization of the salt of (L-Ia) and of the chiral base at the same time as the racemization of the salt of (D-Ia) in one mixture.

The various possibilities for carrying out the racemate resolution according to the invention and the racemization of the acid (D-Ia) or salt thereof according to the invention are explained below.

One possibility comprises, after the crystallization in stage b) of the process according to the invention, heating the mother liquor, which essentially contains the diastereomeric salt of (D-Ia) and residues of the diastereomeric salt of (L-Ia), in the presence of one of the said aldehydes, carrying out the racemization at temperatures of 0°–120° C., preferably 30°–85° C., in particular 35°–75° C. The salt of the racemized amino acid and of the chiral base can then be returned directly, i.e. without working up and without changing the solvent, to the next crystallization batch.

A combined procedure (alternative 1) as batch process or as continuous process for preparing the ammonium salt (L-Ib) starting from the ammonium salt (DL-Ib) comprises, for example, (1) reacting ammonium [DL]-homoalanin-4-yl(methyl)-phosphinate with a chiral base in a solvent mixture of water and an organic solvent which solubilizes the ammonium [DL]-homoalanin-4-yl(methyl)-phosphinate, and removing the liberated ammonia, then (2) at temperatures of 0°–85° C. allowing the diastereomeric salt of [L]-homoalanin-4-yl(methyl)phosphinic acid and of the chiral base to crystallize out of a solvent mixture of water and an organic solvent, and isolating it, for example by filtration with suction, and subsequently (3) heating the mother liquor from the crystals, which essentially contains the other diastereomeric salt of the [D]-amino acid and residues of the diastereomeric salt of the [L]-amino acid, in the presence of a (hetero)aromatic aldehyde at temperatures of 20°–120° C. and, after the racemization, passing the resulting solution to the next crystallization batch (2) and (4) reacting the diastereomeric salt of [L]-homoalanin-4-yl (methyl)phosphonic acid and of the chiral base from stage (2) in the mixture of water and an organic solvent or in the organic solvent itself with ammonia, whereupon ammonium [L]-homoalanin-4-yl-(methyl)phosphinate (L-Ib) precipitates, isolating the precipitated ammonium salt (L-Ib), for example by filtration with suction, and returning the mother liquor, which essentially contains the chiral base, to stage (1) of the next batch.

It is important for optimization of the combined process to adapt the temperatures to the particular process step. Temperatures of 20°–100° C. are advantageous in stage (1), whereas the step according to stage (2) is beneficially carried out at 0°–85° C., preferably at 15°–75° C. The temperature in stage (3) should be appropriate for the reactivity of the aldehyde. The process according to stage (4) can preferably be carried out at temperatures of 0°–60° C.

In another possibility, which is particularly preferred, the racemization is carried out in the same stage as the crystallization of the diastereomeric salt of (L-Ia). The conditions for the crystallization in respect of solvent and temperature are then inevitably consistent with those for the racemization; this restricts the choice of the racemization processes and, in the case of the mentioned racemization with aldehydes, the choice of the possible aldehydes. As already mentioned above, this combined process is not practicable using the conventional processes in the presence of acids and aldehydes but can be carried out using the said inventive process for racemization using specific aldehydes without the addition of acids.

The inventive variant of the combined process comprises reacting a mixture of the diastereomeric salts of D acid and L acid and of the chiral base, dissolved in an aqueous or aqueous-organic solvent in which the salt of the D acid has a higher solubility than the salt of the L acid, at temperatures of 0°–85° C., preferably of 30°–85° C. in the presence of an aldehyde, the temperature being set sufficiently low for the salt of the L acid and of the chiral base to crystallize out at the same time.

It is possible in principle with the preferred combined process (racemate resolution and racemization) to convert (DL-Ia) 100% into (L-Ia). Suitable for the preferred process are the abovementioned chiral bases and the six-membered (hetero) aromatic aldehydes which have a hydroxyl group in position 2 with respect to the aldehyde group and electron-attracting radicals in position 3 or 5 with respect to the aldehyde group, in particular the bases and aldehydes mentioned as preferred.

The preferred combined procedure (alternative 2), as batch process or as continuous process for the preparation of the ammonium salt (L-Ib) starting from the ammonium salt (DL-Ib), comprises, for example, (1') reacting ammonium [DL]-homoalanin-4-yl(methyl)-phosphinate with a chiral base in a solvent mixture of water and an organic solvent which solubilizes the ammonium [DL]-homoalanin-4-yl(methyl)-phosphinate, and removing the ammonia, then (2') reacting with an aromatic aldehyde at temperatures of 0°–85° C., preferably of 30°–85° C. in the presence of a solvent mixture of water and organic solvent and, at the same time, allowing the diastereomeric salt of [L]-homoalanin- 4-yl(methyl)phosphinic acid and of the chiral base to crystallize out, isolating the crystals, for example by filtration with suction, and adding the mother liquor to stage (2') of the next batch and (3') reacting the diastereomeric salt of [L]-homoalanin-4-yl (methyl)phosphinic acid and of the chiral base from stage (2') in the mixture of water and an organic solvent or in the organic solvent itself with ammonia, moreover filtering the precipitated ammonium [L]-homoalanin-4-yl (methyl)phosphinate with suction, and returning the mother liquor, which essentially contains the chiral base, to stage (1') of the next batch.

For the process to succeed it is important that the temperatures are adapted to the particular process step. Process steps (1') and (3') substantially correspond to process steps (1) and (4) from the combined process already mentioned above (alternative 1). The process step according to stage (1') is advantageously carried out at temperatures of 20°–100° C., whereas the step according to stage (2') is beneficially carried out at the temperature at which the diasteromeric salt of (L-Ia) crystallizes out but the racemization of the undesired (D-Ia) still takes place sufficiently quickly. Stage (3') is advantageously carried out at temperatures of 0°–60° C.

A diagrammatic comparison of alternatives 1 and 2 shows, taking the example of the racemate resolution of (L-Ib), the saving of a process stage in alternative 2 (see Table 1):

TABLE 1

| No. | Alternative 1 | Alternative 2 |
|---|---|---|
| (1) | (DL-Ib) + chiral base | (DL-Ib) + chiral base |
| (2) | Removal of NH$_3$, where appropriate change solvent | Removal of NH$_3$, where appropriate change solvent |
| (3) | Crystallization (racemate resolution) | Crystallization (racemate resolution) and reaction with aldehyde |
| (4) | Filtration | Filtration Mother liquor back to (3) |
| (5) | Dissolve crystals and react with NH$_3$ | Dissolve crystals and react with NH$_3$ |
| (6) | Filter off product (L-Ib), mother liquor back to (1) | Filter off product (L-Ib), mother liquor back to (1) |
| (7) | Heat mother liquor from (4) with aldehyde and back to (3) | |

Re Table 1: (No.) = number of the process operation

It is possible to carry out the individual process steps batchwise or else continuously. Mother liquors resulting from the use are preferably returned to the complete process in order to keep losses of yield small.

Suitable solvents for the process stages described above are the solvents already mentioned for the crystallization stage. An advantageous procedure comprises using the same solvent system in all the process steps. However, it is sometimes also sensible to vary the properties of the solvent system simply by adding another solvent to the solvent from the previous stage.

EXAMPLES

In the following Examples, quantity and percentage data are based on weight unless otherwise indicated. The names "L salt", "D salt" and "D,L salt" mean the salt of (L-Ia), (D-Ia) and (D,L-Ia), respectively, and of the chiral base.

Example 1

1.1 39.6 g of 99.8% pure ammonium [DL]-homoalanin-4-yl-(methyl)phosphinate (0.2 mole) and 65.5 g of (−)quinine (99% pure) (0.2 mole) are heated to reflux in 210.8 g of water. Subsequently 22.6 g of aqueous ammonia are removed by applying a reduced pressure of 100 mbar. At 70° C., 766.4 g of tert-butanol and then 3.38 g of 5-nitrosalicylaldehyde (0.02 mole) are added, and the clear solution is seeded at 50° C. with [L]-homoalanin-4-yl(methyl)-phosphinic acid/quinine salt. The diastereomeric L salt precipitates slowly at 48° C. and below. The mixture is allowed to reach room temperature over the course of 6 hours, and the solid is filtered off with suction, washed with a little tert-butanol/water (80:20) and dried in vacuo at 60° C. This results in 41.0 g of [L]-homoalanin-4-yl(methyl)-phosphinic acid/quinine salt with a purity of L salt:D salt of 98.7:1.3.

1.2 The mother liquor from Example 1.1 is refluxed for 9 hours (sample measurement L:D=50.6:49.4) and added to another 0.2 mole batch in analogy to Example 1.1 at 70° C. (amount used about 0.319 mole of [DL] salt). Crystallization is allowed to occur, and 97.3 g of [L]-homoalanin-4-yl(methyl)phosphinic acid/quinine salt are obtained with a purity of L salt:D salt of 99.5:0.5 (corresponding to 60% of theory). The mother liquor can in turn be added to another batch. The crystals are taken up in 97.3 g of methanol, and 27.8 g of methanolic ammonia (17.7% strength) (0.29 mole) are added; the crystals which have formed are then filtered off. 36.2 g of ammonium [L]-homoalanin-4-yl(methyl)phosphinate are obtained with an optical purity of L:D=99.5:0.5. This corresponds to an isolated yield of 57.0% of theory based on 0.319 mole of DL salt. The mother liquor from these crystals, which essentially contains the (−)quinine, is added to another batch.

Example 2

39.6 g of 99.8% pure ammonium [DL]-homoalanin-4-yl-(methyl)phosphinate (0.2 mole) and 65.5 g of (−)quinine (99% pure) (0.2 mole) are heated in 210.8 g of water; subsequently 24.0 g of aqueous ammonia are removed by applying a reduced pressure of 100 mbar. At 70° C., 766.4 g of tert-butanol and then 4.3 g of 3,5-dinitrosalicylaldehyde (0.02 mole) are added, the mixture is cooled to 50° C. and the clear solution is seeded with [L]-homoalanin-4-yl (methyl)phosphinic acid/quinine salt. The mixture is stirred for 9 to 10 hours, during which the L salt slowly precipitates. The mixture is allowed to reach room temperature over the course of 6 hours, and the solid is filtered off with suction, washed with tert-butanol/water (80:20) and dried in vacuo at 60° C. This results in 86.5 g of [L]-homoalanin-4-yl(methyl)-phosphinic acid/quinine salt with a purity of L salt:D salt of 99.5:0.5. This corresponds to a yield of 85.1% of theory. The mother liquor is added to another batch at 70° C. The crystals are taken up in 86.5 g of methanol, 24.7 g of methanolic ammonia (17.7% strength) (0.258 mole) are added, and the crystals which form are filtered off. 32.2 g of ammonium [L]-homoalanin-4-yl-(methyl)phosphinate are obtained with an optical purity of L:D=99.9:1.0. This corresponds to an isolated yield of 80.5% of theory. The mother liquor, which essentially contains the (−)quinine, is added to another batch.

Example 3

3.5 g of ammonium [DL]-homoalanin-4-yl(methyl) phosphinate (0.019 mole) and 6.2 g of (−)quinine (0.019 mole) are dissolved in 18.2 g of water at 50° C., and 27.4 g of hot acetone are added. A clear solution is obtained at 50° C. It is allowed to cool slowly while seeding the clear solution with [L]-homoalanin-4-yl(methyl)phosphinic acid/ quinine salt, and crystallization is allowed to occur. The solid is filtered off with suction at 20° C. and washed with a little acetone, and the filter cake is dried at 60° C. in vacuo. 4.0 g of [L]-homoalanin-4-yl-(methyl)phosphinic acid/ quinine salt which contains L-amino acid portion and D-amino acid portion in the enantiomeric ratio of 99.8:0.2 are obtained. This corresponds to a yield of 83.3% of theory based on the use of L form, and 41.7% of theory based on D,L mixture used.

Example 4

3.5 g of ammonium [DL]-homoalanin-4-yl(methyl) phosphinate (0.019 mole) and 6.2 g of (−)quinine (0.019 mole) are dissolved in 18.2 g of water at 50° C., and 103.1 g of hot isopropanol are added. A clear solution is obtained at 50° C. It is allowed to cool slowly while seeding the clear solution with [L]-homoalanin-4-yl(methyl)phosphinic acid/ quinine salt, and crystallization is allowed to occur. The solid is filtered off with suction at 20° C. and washed with a little acetone, and the filter cake is dried at 60° C. in vacuo. 4.2 g of [L]-homoalanin-4-yl-(methyl)phosphinic acid/ quinine salt which contains L-amino acid portion and D-amino acid portion in the enantiomeric ratio of 99.8:0.2 are obtained. This corresponds to a yield of 86.3% of theory based on the use of L form, and 43.2% of theory based on D,L mixture used.

Example 5

1.1 g of [D]-homoalanin-4-yl(methyl)phosphinic acid (D:L=99.5:0.5) (0.006 mole), 2.0 g of quinine (0.006 mole) and 0.13 g of 3,5-dinitrosalicylaldehyde (0.0006 mole) are dissolved in 5.2 g of water and 23.0 g of tert-butanol and stirred at 40° C. for 23 hours. [DL]-homoalanin-4-yl (methyl)phosphinic acid/quinine salt which contains D-amino acid portion and L-amino acid portion in the enantiomer ratio of 50.2:49.8 is obtained.

Example 6

0.8 g [L]-tert-leucine (99% pure, 0.006 mole), 2.0 g of quinine (0.006 mole) and 0.13 g of 3,5-dinitrosalicylaldehyde (0.0006 mole) are dissolved in 5.2 g of water and 23.0 g of tert-butanol and stirred at 50° C. for 24 hours. [DL]-tert-leucine which contains D-amino acid portion and L-amino acid portion in the enantiomer ratio of 50.9:49.1 is obtained.

Example 7

3.44 g of [DL]-homoalanin-4-yl(methyl)phosphinic acid and 5.6 g of cinchonine (0.019 mole) are dissolved in 27 ml of water at 50° C., and 243 g of tert-butanol are added hot. The solution is seeded with [D]-homoalanin-4-yl-(methyl) phosphinic acid and slowly cooled to room temperature. 4.5 g of [D]-homoalanin-4-yl(methyl)phosphinic acid/ cinchonine salt are obtained with an enantiomeric purity of D:L=96.7:3.3. This corresponds to an isolated yield of 96.2% of theory.

Comparative Examples

A) 90 g of tert-butanol are added to 2.7 g of [DL]-homoalanin-4-yl(methyl)phosphinic acid (0.015 mole), 5.0 g of ammonium (+)-3-bromocamphor-8-sulfonate (0.015 mole) in 10 g of demineralized water at 75° C. in such a way that the temperature is kept at 75° C. The mixture is heated under reflux for 1 hour and then slowly allowed to reach room temperature. Precipitated crystals are filtered off with suction, washed and dried in vacuo at 50° C. 4.8 g of homoalanin-4-yl(methyl)phosphinic acid/ (+)-3-bromocamphor-8-sulfonic acid salt are obtained with a diastereomer content of L:D=50:50.

B) 3.0 g of ammonium [DL]-homoalanin-4-yl(methyl)-phosphinate (0.015 mole), 5.0 g of ammonium (+)-3-bromocamphor-8-sulfonate (0.015 mole) are dissolved in 10 g of demineralized water at 75° C. and, at this temperature, 135 g of tert-butanol are added. 1.53 g of $H_2SO_4$ (96% strength) (0.015 mole) are added, and the mixture is allowed to cool slowly. 3.5 g of homoalanin-4-yl(methyl)phosphinic acid/(+)-3-bromocamphor-8-sulfonic acid salt with a diastereomer content of L:D= 50.1:49.9 are obtained.

C) 2.9 g of [D]-homoalanin-4-yl(methyl)phosphinic acid/ quinine salt with a D salt:L salt purity of 99.8:0.2 (0.0057 mole), 0.07 g of salicylaldehyde, 6.2 g of acetic acid and 0.02 g of water are stirred at 50° C. for 8 hours. The solution obtained in this way contains the racemic salt in a diastereomer ratio of L salt:D salt =49.8:50.2.

D) 6.2 g of quinine, 3.44 g of [DL]-homoalanin-4-yl-(methyl)phosphinic acid in 20 ml of acetic acid and 80 ml of methyl isobutyl ketone are heated and slowly cooled to room temperature. During this, 3.1 g of [DL] salt of diastereomer ratio L:D=49.6:50.4 crystallize out.

We claim:

1. A salt of [L]- or [D]-homoalanin-4-yl(methyl) phosphinic acid and chiral alkaloid bases.

2. A salt of [L]-homoalanin-4-yl(methyl)phosphinic acid (L acid) and quinine.

3. The salt of [L]- or [D]-homoalanin-4-yl(methyl) phosphinic acid according to claim 1 wherein the chiral alkaloid base is quinine, cinchonidine, and brucine.

4. The salt of [L]- or [D]-homoalanin-4-yl(methyl) phosphinic acid according to claim 1, wherein the chiral alkaline base is quinine.

5. The salt of [L]- or [D]-homoalanin-4-yl(methyl) phosphinic acid according to claim 1, wherein the chiral alkaline base is cinchonidine.

6. The salt of [L]- or [D]-homoalanin-4-yl(methyl) phosphinic acid according to claim 1, wherein the chiral alkaline base is brucine.

7. The salt according to claim 3, wherein the homoalanin-4-yl(methyl)phosphinic acid is in the [D]-homoalanin-4-yl (methyl)phosphinic acid.

8. The salt according to claim 7, which is [D]-homoalanin-4-yl(methyl)phosphinic acid and quinidine.

9. The salt according to claim 7, which is [D]-homoalanin-4-yl(methyl)phosphinic acid and cinchonine.

* * * * *